(12) United States Patent
Chang et al.

(10) Patent No.: US 8,086,020 B2
(45) Date of Patent: Dec. 27, 2011

(54) SYSTEM AND METHOD FOR ANALYZING IMPURITIES OF AN OBJECT

(75) Inventors: Chih-Kuang Chang, Taipei Hsien (TW); Xian-Yi Chen, Shenzhen (CN); Yi-Rong Hong, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 636 days.

(21) Appl. No.: 12/253,931

(22) Filed: Oct. 17, 2008

(65) Prior Publication Data

US 2009/0161940 A1    Jun. 25, 2009

(30) Foreign Application Priority Data

Dec. 24, 2007   (CN) .............................. 200710203360

(51) Int. Cl.
G06K 9/00   (2006.01)

(52) U.S. Cl. ...................................................... 382/141

(58) Field of Classification Search .................. 382/141, 382/149

See application file for complete search history.

(56) References Cited

U.S. PATENT DOCUMENTS

| | | | | |
|---|---|---|---|---|
| 5,608,816 | A * | 3/1997 | Kawahara et al. | 382/149 |
| 6,567,168 | B2 * | 5/2003 | Nara et al. | 356/394 |
| 2006/0018530 | A1 * | 1/2006 | Oaki et al. | 382/144 |

* cited by examiner

Primary Examiner — Michael A Lyons
Assistant Examiner — Jonathan Hansen
(74) Attorney, Agent, or Firm — Altis Law Group, Inc.

(57) ABSTRACT

A computer-implemented method for analyzing impurities of an object is provided. The method includes selecting a region from an image of the object, pre-treating the region to calculate a threshold, processing the region and deleting the points from an outer layer of the region. The method further includes setting a starting point and search directions, determining a point before a first boundary point as an origin of the region and searching the next boundary points if the first boundary point has been searched. The method also includes searching all the boundary points in the region, forming an impurity if the last boundary point coincides with the first boundary point, seed filling the impurity and calculating an area value, and comparing the area value with an allowable area value to determine whether the impurity satisfies impurity specifications.

17 Claims, 7 Drawing Sheets

SYSTEM AND METHOD FOR ANALYZING IMPURITIES OF AN OBJECT

BACKGROUND

1. Field of the Invention

Embodiments of the present disclosure relate to systems and methods for analyzing images, and more particularly, to a system and method for analyzing impurities of an object in an image.

2. Description of Related Art

Product quality has long been one of the most important factors in maintaining a typical manufacturing enterprises' competitiveness. Ways of improving the quality of products is an important ongoing pursuit of such enterprises. It is essential to verify the correctness of an object before a batch production of the object.

In recent years, a user can use an image measuring machine installed with a charge coupled device (CCD) to obtain an image of an object by scanning the object, subsequently converting the image into a digital file. The quality of the object may be determined by checking whether any impurities exist in the digital file of the object. When the image measuring machine measures the object, traditional methods cannot correctly calculate an area value of the object due to irregular shape of the object, especially for objects with a significant number of impurities.

What is needed, therefore, is a system and method for analyzing impurities of an object, which can search and correctly analyze all the impurities of the object in an image.

SUMMARY

A computer-implemented method for analyzing impurities of an object is provided. The method includes: (a) selecting a region from an image of the object; (b) pre-treating the region to calculate a threshold of the region; (c) performing a binary image processing on the region according to the threshold, performing an edge processing to extract and identify points in the region, and deleting the points from the outer layer of the region; (d) setting a starting point in the region and setting search directions to search all boundary points in the region; (e) determining whether a first boundary point has been searched; (f) in response to a first boundary point has been searched, determining a point before the first boundary point as an origin of the region and searching the next boundary points along the search directions; (g) searching all the boundary points in the region by repeating block (f) until the last boundary point has been searched, and determining whether the last boundary point and the first boundary point coincide; (h) forming an impurity by all the boundary points if the last boundary point coincides with the first boundary point; (i) seed filling the impurity and calculating an area value of the impurity; (j) comparing the area value with an allowable area value to determine whether the impurity complies with specified impurity specifications; and (k) generating an analysis result according to the comparison results, and storing the analysis result in a storage system.

Other advantages and novel features will become more apparent from the following detailed description certain embodiments of the present disclosure when taken in conjunction with the accompanying drawings.

DETAILED DESCRIPTION OF CERTAIN INVENTIVE EMBODIMENTS

All of the processes described below may be embodied in, and fully automated via, software code modules executed by one or more general purpose computers or processors. The code modules may be stored in any type of computer-readable medium or other computer storage device. Some or all of the methods may alternatively be embodied in specialized computer hardware.

Figure 1:
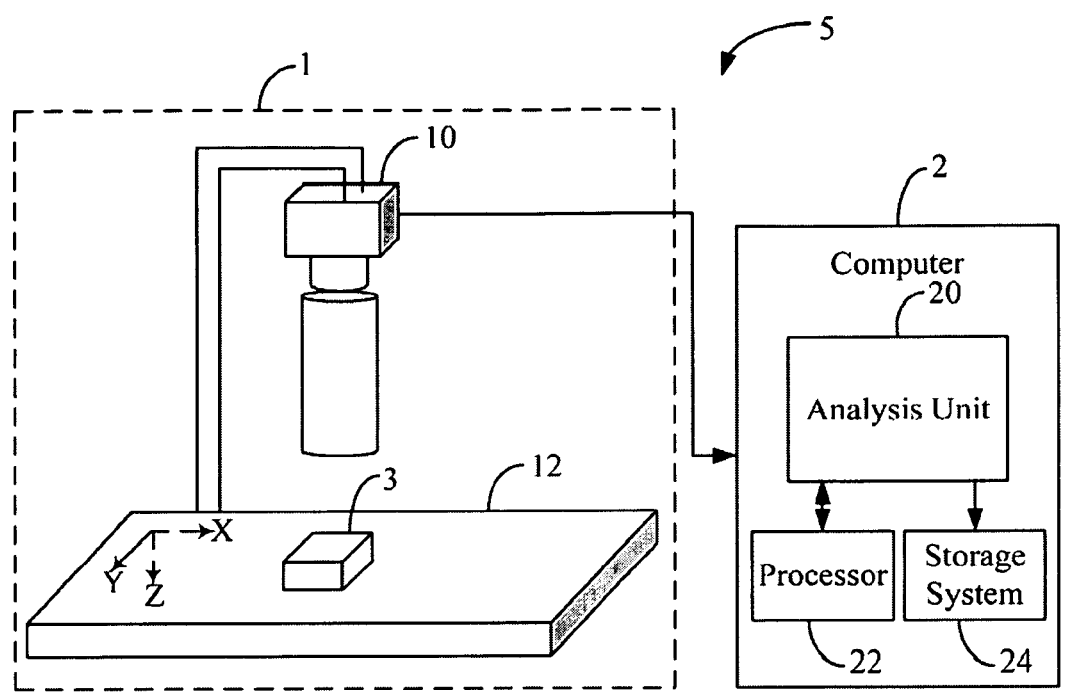
FIG. 1 is a block diagram of one embodiment of a system for analyzing impurities of an object.

FIG. 1 is a block diagram of one embodiment of a system 5 for analyzing impurities of an object (hereinafter, "the system 5"). In one embodiment, the system 5 includes an image measuring machine 1, and a computer 2 electrically connected with the image measuring machine 1. The image measuring machine 1 typically includes a charge coupled device (CCD) 10 and a platform 12. The CCD 10 is configured for obtaining an image of an object 3 that is put on the platform 12. The computer 2 comprises an analysis unit 20, at least one processor 22, and a storage system 24. The analysis unit 20 is configured for selecting a region to be analyzed from the image of the object 3 and determining whether impurities of the region comply with specified impurity specifications. The specified impurity specifications include an allowable area value, an allowable number of impurities of the object 3, and an allowable distance between every two adjacent impurities. When all the impurities of the object 3 comply with the specified impurity specifications, the analysis unit 20 may determine that the quality of the object 3 is eligible.

In another embodiment, the selected region may include a desired hole or any other composition parts of the object so as to reduce error in determining impurities of the object. Before the analysis unit 20 analyzes the region, the analysis unit 20 may remove the desired hole and the composition parts, which are not the impurities, from the image of the object 3 according to user demands. For example, the analysis unit 20 removes a corresponding graphic of the desired hole from the image of the object 3. The analysis unit 20 only analyzes the impurities of the object 3 in the region below.

Figure 2:
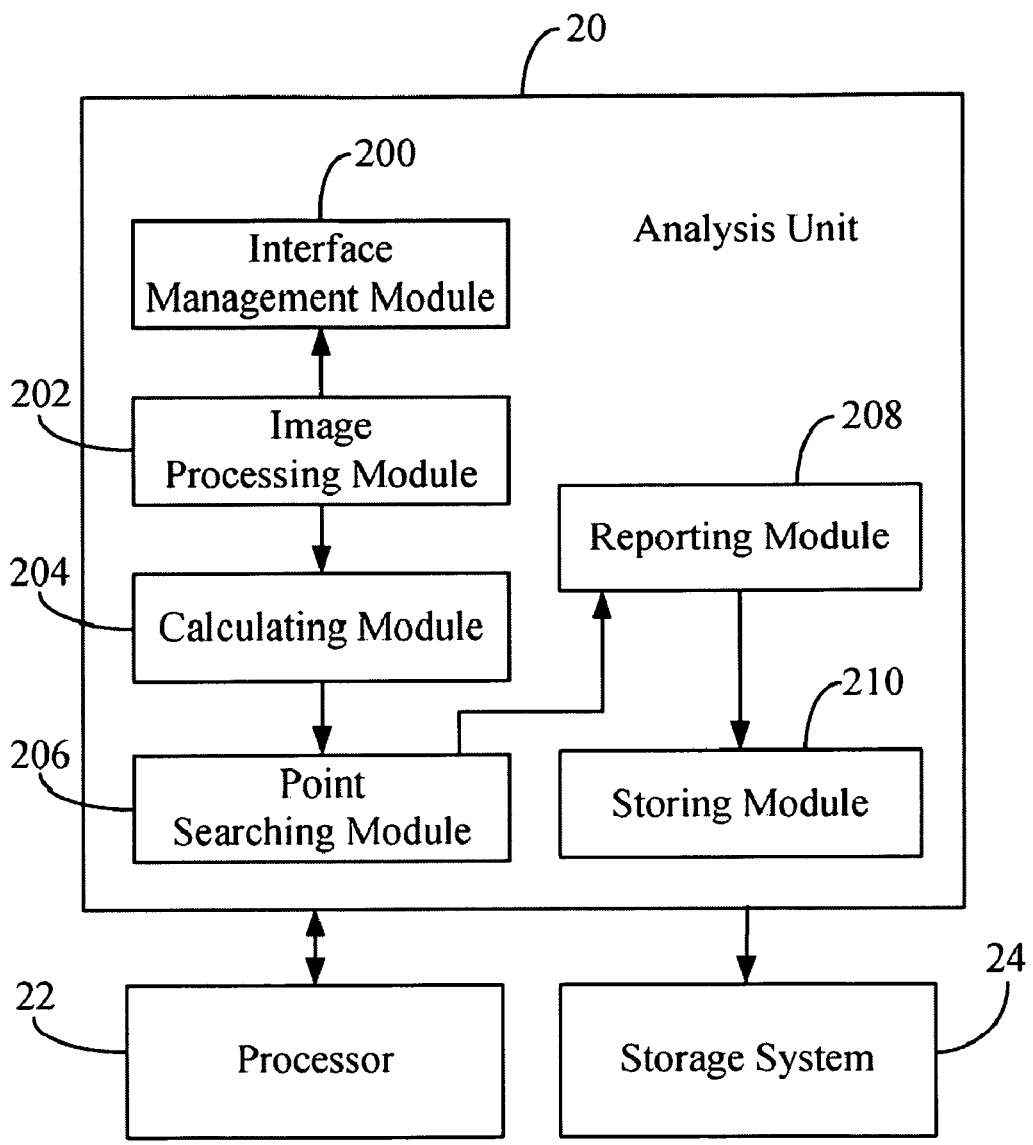
FIG. 2 is a block diagram of one embodiment of an analysis unit of FIG. 1.

FIG. 2 is a block diagram of one embodiment of the analysis unit 20 of FIG. 1. The analysis unit 20 may include a plurality of instructions, and executed by the processor 22 of the computer 2. In one embodiment, the analysis unit 20 may include an interface management module 200, an image processing module 202, a calculating module 204, a point searching module 206, a reporting module 208, and a storing module 210.

The interface managing module 200 is configured for managing a plurality of interface styles and region analysis tools. A user can select a favorite operation interface from the plurality of interface styles. In the embodiment, the region analysis tools may include a region selecting tool that is used for selecting a region from the image of the object 3.

While the CCD 10 obtains the image of the object 3, image noises and uneven gray-level distribution can be generated easily because of light sources and other external factors. As a result, the image processing module 202 needs to pre-treat the region, such by means of a mean filtering, a median filtering, an edge preserving filtering, and a Gaussian filtering.

Figure 3:
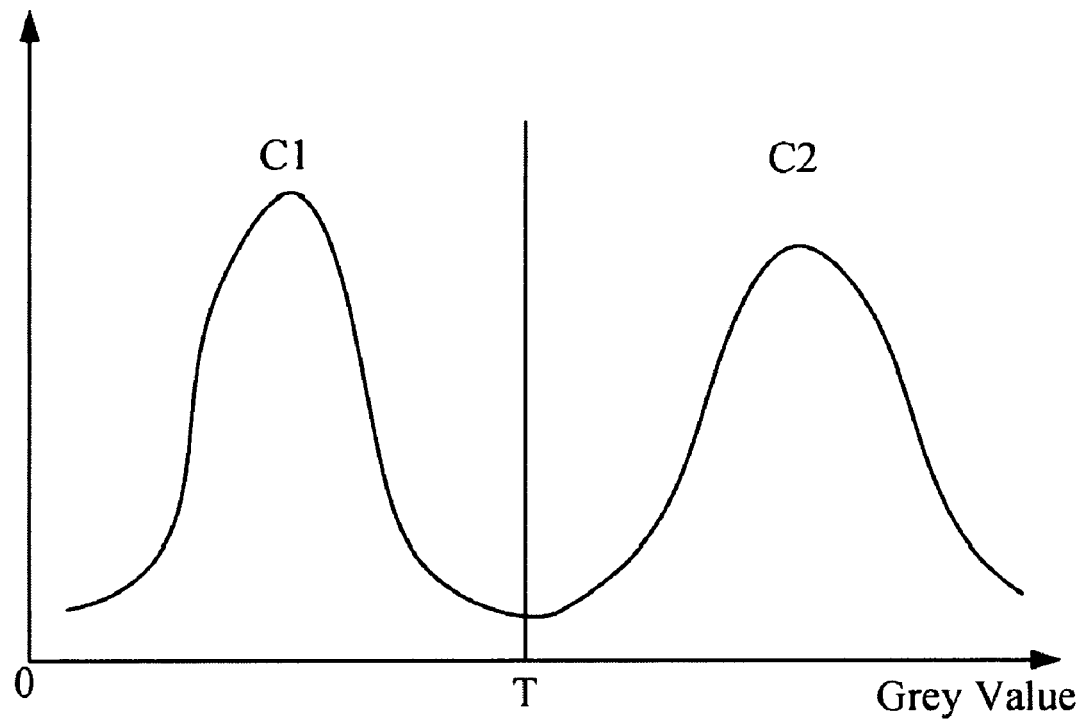
FIG. 3 is a schematic and graph diagram of grey values.

The calculating module 204 is configured for calculating a threshold of the region after the region has been pre-treated. With reference to FIG. 3, which shows a schematic and graph diagram of grey values, the point "T" represents the threshold of the region. The threshold, which is a crossover point of the fuzzy enhancement, is determined by the theory of image segmentation, such as the area "C1" and "C2." In computer vision, segmentation refers to the process of partitioning an image into multiple regions (sets of pixels). The goal of image segmentation is to change the representation of the image into something that is more easier to analyze.

The image processing module 202 is further configured for performing a binary image processing on the region according to the threshold in order to enhance the contrast of the image, performing an edge processing to extract and identify points in the region, and deleting the points from an outer layer of the region.

The point searching module 206 is configured for setting a starting point and search directions to search boundary points in the region, considering a point before each of the boundary points as an origin to search the next boundary points according to the search directions. All the boundary points in the region can form an impurity when the first boundary point and the last boundary point coincide.

Figure 4:
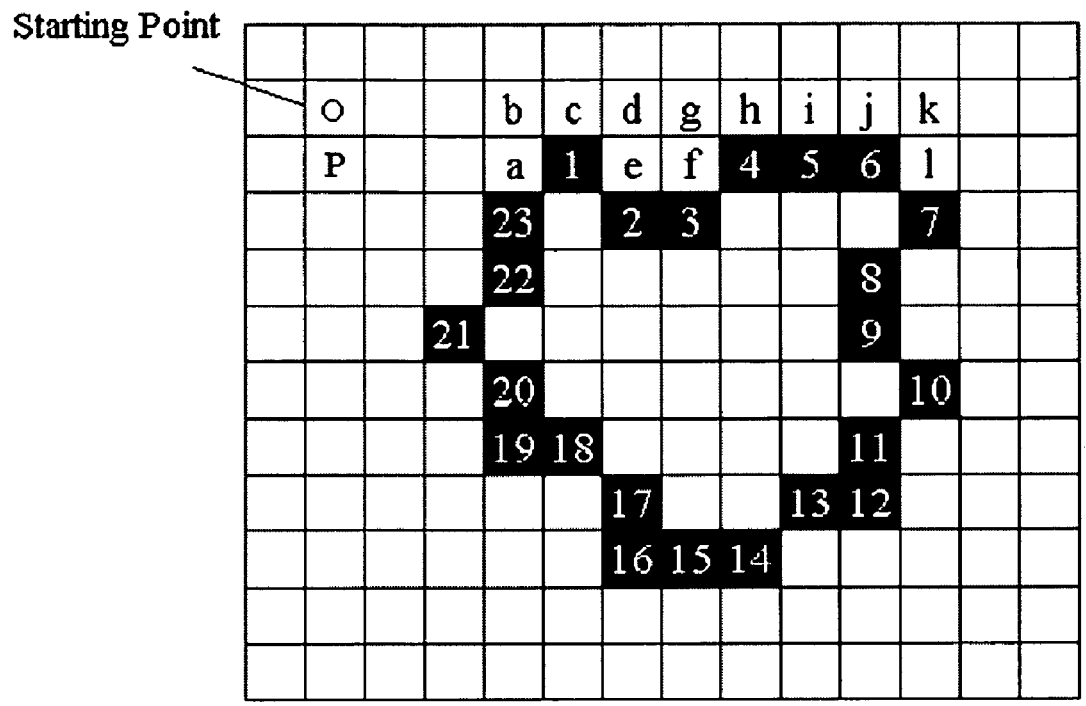
FIG. 4 is a schematic diagram illustrating one embodiment of searching boundary points in a clockwise direction.
Figure 5:
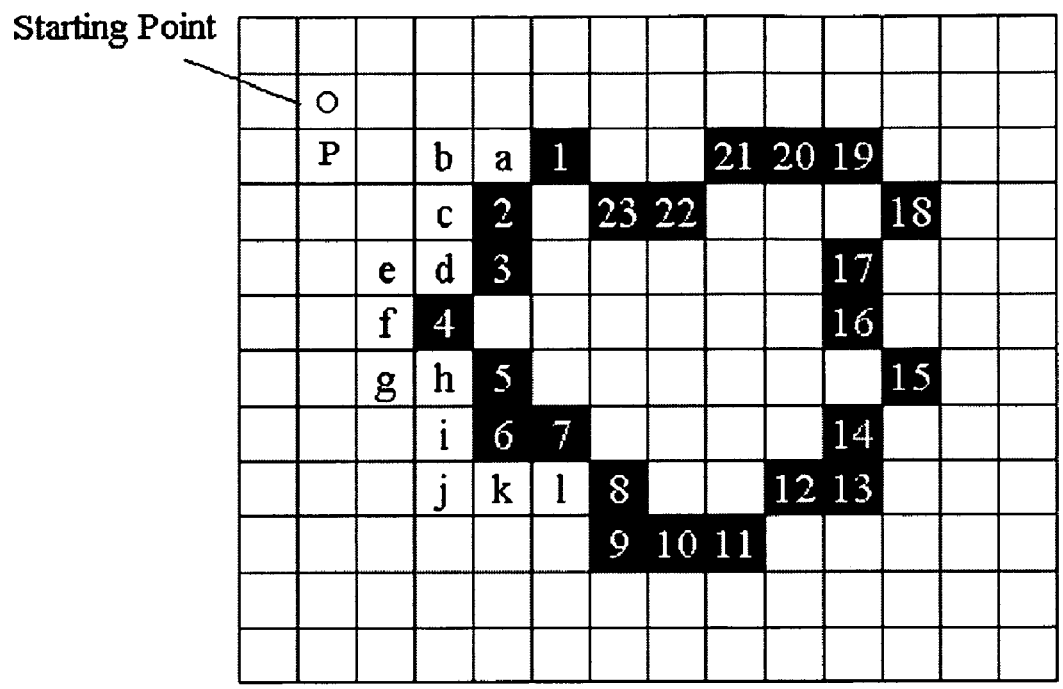
FIG. 5 is a schematic diagram illustrating one embodiment of searching boundary points in a counter-clockwise direction.

In the embodiment, the search directions include a first direction before searching the first boundary point and a second direction after any boundary point has been searched. The first direction is a direction of searching towards the left side or a direction of searching towards the right side. The second direction is a clockwise direction or a counter-clockwise direction. As illustrated in FIG. 4 and FIG. 5, the search directions are different.

Figure 6:
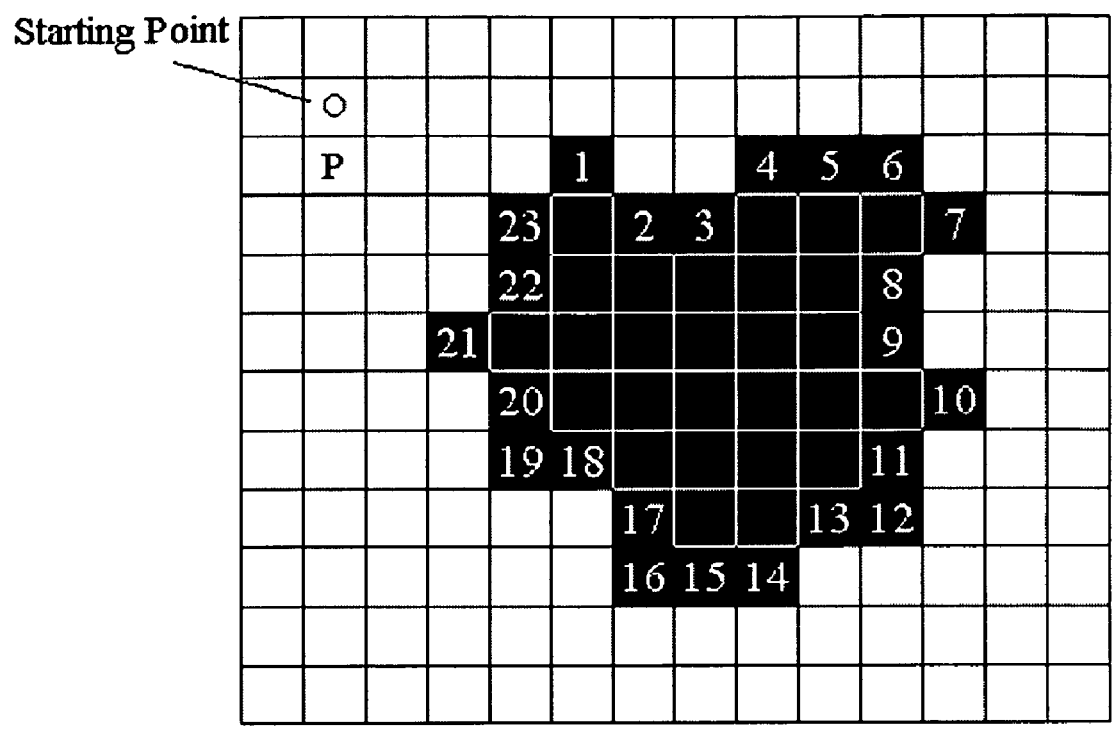
FIG. 6 is a schematic diagram illustrating one embodiment of seed filling an impurity.

The calculating module 204 is further configured for seed filling the impurity to find all points in the region by a path of target colors and change the points to the target colors, and calculating an area value of the impurity based on the points. The method of seed filling is illustrated in FIG. 6. The reporting module 208 is configured for comparing the area value with the allowable area value to determine whether the impurity complies with the specified impurity specifications, and generating an analysis result according to the comparison results.

The storing module 210 is configured for storing the analysis result in the storage system 24. In one embodiment, the storage system 24 is at least one of a hard disk drive, a compact disc, a digital video disc, and a tape drive.

In one embodiment, the point searching module 206 is further configured for searching all the impurities of the object 3 in the image. The calculating module 204 counts a total number of the impurities, and calculates an area value of each of the impurities and a distance between every two adjacent impurities. The reporting module 208 determines whether the quality of the object 3 is eligible by comparing the total number of the impurities with the allowable number, by comparing the area value of each of the impurities with the allowable area value and by comparing the distance between every two adjacent impurities with the allowable distance. The reporting module 208 further generates an analysis report according to the determination result. The storing module 210 stores the analysis report in the storage system 24.

In another embodiment, the calculating module 204 further calculates the area value of the region, calculates a ratio of each of the impurities to the region, and calculates a perimeter of each of the impurities. The reporting module 208 compares the ratio of each of the impurities with the allowable ratio, compares the perimeter of each of the impurities with the allowable perimeter, and reports the comparison results that can also determine whether the quality of the object 3 is eligible.

With references to FIG. 4 and FIG. 5, the point searching module 206 may set the starting point and search directions to search the boundary points in each region. As illustrated in both FIG. 4 and FIG. 5, a point "O" represents the starting point. The first direction in both FIG. 4 and FIG. 5 is the direction of searching towards the right side. The second direction in FIG. 4 is the clockwise direction, while the second direction in FIG. 5 is the counter-clockwise direction. If no boundary point has been searched in a row beginning with the starting point "O," the point searching module 206 determines the point "P" as an origin to search the boundary points. The point "P" is under the starting point "O." After a first boundary point "1" has been searched, the point searching module 206 determines a point "a" before the first boundary point "1" as the origin to search the next boundary points according to the search direction. Namely, in FIG. 4, the point searching module 206 searches a second boundary point "2" along the direction of "a→b→c→d→e→2," and determines the point "e" as the origin to search the third boundary point "3" along the direction of "e→f→3"; In FIG. 5, the point searching module 206 searches a second boundary point "2" along the direction of "a→b→c→2," and determines the point "c" as the origin to search the third boundary point "3" along the direction of "c→d→3." By this way, the point searching module 206 has searched twenty-three boundary points in both FIG. 4 and FIG. 5. The last boundary point (namely the twenty-third boundary point) coincides with the first boundary point "1," and all the twenty-three boundary points form the impurity.

With reference to FIG. 6, the calculating module 204 seed fills the impurity. Each point within the region is clearly displayed to the user after the seed filling, which can also be considered a pixel point. The calculating module 204 calculates an area value "S" of the impurity by using a formula. In one embodiment, the formula may be defined as S=S0*N, wherein "S0" represents an area value of one pixel point, "N" represents a total number of pixel points in the region. For example, if the magnification of the CCD 10 is "100," the area value S0=(1/100)*(1/100)=0.0001 square millimeters. FIG. 6 shows fifty pixel points in one exemplary embodiment, so the area value S=0.0001*50=0.005 square millimeters. In another embodiment, the calculating module 204 can also calculate the area value of the region, the ratio of the impurity to the region, and the perimeter of the impurity.

Figure 7:
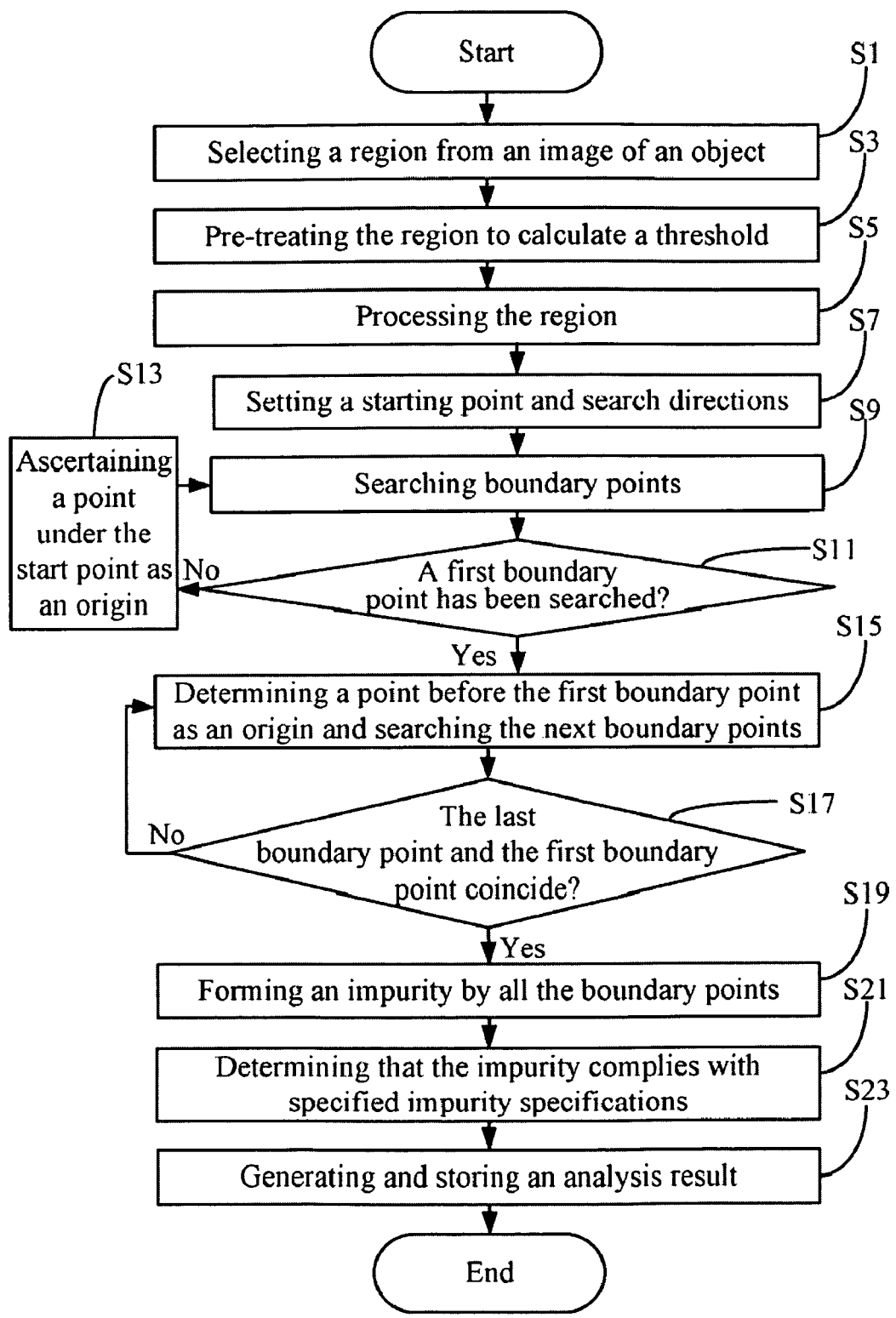
FIG. 7 is a flowchart of one embodiment of a method for analyzing impurities of an object.

FIG. 7 is a flowchart of one embodiment of a method for analyzing impurities of the object 3. Depending on the embodiment, additional blocks may be added, while others removed, and the ordering of the blocks may also be changed. Before the flow of analyzing the impurities, the CCD 10 needs to obtain an image of the object 3.

In block S1, the interface management module 200 uses the region selecting tool to select a region from the image of the object 3. The region may include at least one impurity. In the embodiment, only one impurity included in the region is given as an example to illustrate the method.

In block S3, the image processing module 202 pre-treats the region to calculate a threshold of the region, such by means of a mean filtering, a median filtering, an edge preserving filtering, and a Gaussian filtering. After the pre-treating, image noises of the region can be reduced and uneven gray-level distribution can be eliminated.

In block S5, the image processing module 202 processes the region according to the threshold, such as performing a binary image processing, performing an edge processing and deleting the points from an outer layer of the region. The processed region is shown in FIG. 4 and FIG. 5.

In block S7, the point searching module 206 sets a starting point and search directions, for example, the starting point "O" in both FIG. 4 and FIG. 5. In the embodiment, the search directions include a first direction before searching the first boundary point and a second direction after any boundary point has been searched.

In block S9, the point searching module 206 searches all boundary points in the region according to the starting point and search directions.

In block S11, the point searching module 206 determines whether a first boundary point has been searched. If the first boundary point has been searched, the flow directly enters into block S11. Otherwise, if the first boundary point has not been searched, the flow enters into block S13.

In block S13, the point searching module 206 determines a point under the starting point as an origin and the flow returns block S9 to search the boundary points.

In block S15, the point searching module 206 determines a point before the first boundary point as the origin and searches the next boundary points along the search directions until the last boundary point has been searched.

In block S17, the point searching module 206 determines whether the last boundary point and the first boundary point coincide. If the last boundary point does not coincide with the first boundary point, the flow returns block S15 to continue searching the boundary points. Otherwise, if the last boundary point coincides with the first boundary point, the flow enters into block S19.

In block S19, all the boundary points form an impurity in the region, the calculating module 204 seed fills the impurity and calculates an area value of the impurity. The method of seed filling the impurity and the method of calculating the area value are illustrated in FIG. 6.

In block S21, the reporting module 208 compares the area value with the allowable area value to determine whether the impurity complies with the specified impurity specifications, and generates an analysis result according to the comparison results. In one embodiment, the reporting module 208 determines that the impurity does not comply with the specified impurity specifications if the area value is more than the allowable area value. In another embodiment, the reporting module 208 determines that the impurity complies with the specified impurity specifications if the area value is no more than the allowable area value.

In block S23, the storing module 210 stores the analysis result in the storage system 24.

In another embodiment, the interface management module 200 may repeat the flow of block S3 to block S23 until all parts in the image have been analyzed, to determine whether the quality of the object 3 is eligible. The reporting module 208 reports the determination result, and generates an analysis report according to the determination result. The storing module 210 stores the analysis report to the storage system 24.

Although certain inventive embodiments of the present disclosure have been specifically described, the present disclosure is not to be construed as being limited thereto. Various changes or modifications may be made to the present disclosure without departing from the scope and spirit of the present disclosure.

What is claimed is:

1. A computer-implemented method for analyzing impurities of an object using a computer that is electronically connected to an image measuring machine, the method comprising:

(a) obtaining an image of the object by a charge coupled device of the image measuring machine, and selecting a region from the image of the object;

(b) pre-treating the region by means of a mean filtering, a median filtering, an edge preserving filtering, and a Gaussian filtering, and calculating a threshold of the region;

(c) performing a binary image processing on the region according to the threshold, performing an edge processing to extract and identify points in the region, and deleting the points from an outer layer of the region;

(d) setting a starting point in the region and setting search directions to search all boundary points in the region, the search directions comprising a first direction before searching the first boundary point and a second direction after any boundary point has been searched;

(e) determining whether a first boundary point has been searched;

(f) upon the condition that a first boundary point has been searched, determining a point before the first boundary point as an origin of the region and searching the next boundary points along the search directions;

(g) searching all the boundary points in the region by repeating block (f) until the last boundary point has been searched, and determining whether the last boundary point and the first boundary point coincide;

(h) forming an impurity by all the boundary points upon the condition that the last boundary point coincides with the first boundary point;

(i) seed filling the impurity and calculating an area value of the impurity;

(j) comparing the area value with an allowable area value to determine whether the impurity complies with specified impurity specifications; and (k) generating an analysis result according to the comparison results, and storing the analysis result in a storage system of the computer.

2. The method according to claim 1, wherein the block (e) comprises:
 determining the point under the starting point as the origin of the region to search the boundary points upon the condition that no boundary point has been searched.

3. The method according to claim 1, wherein the first direction is a direction of searching towards left side or a direction of searching towards right side, and the second direction is a clockwise direction or a counter-clockwise direction.

4. The method according to claim 1, wherein the specified impurity specifications comprise an allowable number of impurities of the object, and an allowable distance between every two adjacent impurities.

5. The method according to claim 4, further comprising:
 searching all impurities of the object by repeating block (a) to block (k);
 counting a total number of the impurities, calculating the area value of each of the impurities, and calculating a distance between every two adjacent impurities; and
 determining whether the quality of the object is eligible by comparing the total number of the impurities with the allowable number, by comparing the area value of each of the impurities with the allowable area value and by comparing the distance between every two adjacent impurities with the allowable distance.

6. A computer for analyzing impurities of an object, the computer being electronically connected to an image measuring machine, the computer comprising:

an interface managing module operable to obtain an image of the object by a charge coupled device of the image measuring machine, and manage a region analysis tool for a user to select a region from the image of the object;

an image processing module operable to pre-treat the region to calculate a threshold of the region, performing a binary image processing on the region according to the threshold, performing an edge processing to extract and identify points in the region, and deleting the points from an outer layer of the region;

a point searching module operable to set a starting point in the region and search directions to search boundary points in the region, determining a point before each of the boundary points as an origin of the region to search the next boundary points according to the search directions, and forming an impurity by all the boundary points, the search directions comprising a first direction before searching the first boundary point and a second direction after any boundary point has been searched;

a calculating module further operable to calculate the threshold of the region, seed filling the impurity to find all points in the region, and calculating an area value of the impurity based on the points;

a reporting module operable to compare the area value with an allowable area value to determine whether the impurity complies with specified impurity specifications, and generating an analysis result according to the comparison results;

a storing module operable to store the analysis result in a storage system of the computer; and at least one processor that executes the interface managing module, the image processing module, the point searching module, the calculating module, the reporting module, and the storing module.

7. The computer according to claim 6, wherein the storage system is at least one of a hard disk drive, a compact disc, a digital video disc, and a tape drive.

8. The computer according to claim 6, wherein the first direction is a direction of searching towards left side or a direction of searching towards right side, and the second direction is a clockwise direction or a counter-clockwise direction.

9. The computer according to claim 6, wherein the specified impurity specifications comprise an allowable number of impurities of the object, and an allowable distance between every two adjacent impurities.

10. The computer according to claim 9, wherein the point searching module is further configured for searching all the impurities of the object, and the calculating module is further configured for counting a total number of the impurities, calculating an area value of each of the impurities and calculating a distance between every two adjacent impurities.

11. The computer according to claim 10, wherein the reporting module is further configured for determining whether the quality of the object is eligible by comparing the total number of the impurities with the allowable number, by comparing the area value of each of the impurities with the allowable area value and by comparing the distance between every two adjacent impurities with the allowable distance.

12. The computer according to claim 6, wherein the point searching module forms the impurity upon the condition that the last boundary point coincides with the first boundary point.

13. A non-transitory computer-readable medium having stored thereon instructions that, when executed by a computer, causes the computer to perform a method for analyzing impurities of an object, the method comprising:

(a) obtaining an image of the object by a charge coupled device of an image measuring machine, and selecting a region from the image of the object;

(b) pre-treating the region to calculate a threshold of the region;

(c) performing a binary image processing on the region according to the threshold, performing an edge processing to extract and identify points in the region, and deleting the points from an outer layer of the region;

(d) setting a starting point in the region and search directions to search all boundary points in the region, the search directions comprising a first direction before searching the first boundary point and a second direction after any boundary point has been searched;

(e) determining whether a first boundary point has been searched;

(f) upon the condition that a first boundary point has been searched, determining a point before the first boundary point as an origin of the region and searching the next boundary points along the search directions;

(g) searching all the boundary points in the region by repeating block (f) until the last boundary point has been searched, and determining whether the last boundary point and the first boundary point coincide;

(h) forming an impurity by all the boundary points upon the condition that the last boundary point coincides with the first boundary point;

(i) seed filling the impurity and calculating an area value of the impurity;

(j) comparing the area value with an allowable area value to determine whether the impurity complies with specified impurity specifications; and (k) generating an analysis result according to the comparison results, and storing the analysis result in a storage system of the computer.

14. The non-transitory computer-readable medium according to claim 13, wherein the block (e) comprises:
determining the point under the starting point as the origin of the region to search the boundary points upon the condition that no boundary point has been searched.

15. The non-transitory computer-readable medium according to claim 13, wherein the first direction is a direction of searching towards left side or a direction of searching towards right side, and the second direction is a clockwise direction or a counter-clockwise direction.

16. The non-transitory computer-readable medium according to claim 13, wherein the specified impurity specifications further comprise an allowable number of impurities of the object, and an allowable distance between every two adjacent impurities.

17. The non-transitory computer-readable medium according to claim 16, wherein the method further comprises:
searching all impurities of the object by repeating block (a) to block (k);
counting a total number of the impurities, and calculating an area value of each of the impurities and a distance between every two adjacent impurities; and
determining whether the quality of the object is eligible by comparing the total number of the impurities with the allowable number, by comparing the area value of each of the impurities with the allowable area value and by comparing the distance between every two adjacent impurities with the allowable distance.

* * * * *